(12) United States Patent
Malkani

(10) Patent No.: US 7,785,255 B2
(45) Date of Patent: Aug. 31, 2010

(54) LIGAMENT PROTECTION INSTRUMENTS

(75) Inventor: Arthur Lalit Laxman Malkani, Prospect, KY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1158 days.

(21) Appl. No.: 10/977,419

(22) Filed: Oct. 29, 2004

(65) Prior Publication Data

US 2006/0095042 A1 May 4, 2006

(51) Int. Cl.
*A61B 1/32* (2006.01)
(52) U.S. Cl. ............ 600/235; 600/213; 600/214; 600/219; 600/227; 606/86 R
(58) Field of Classification Search .......... 606/53, 606/74, 86, 105, 157; 600/227, 228, 235, 600/96, 213, 219; 623/13.11, 13.14
See application file for complete search history.

(56) References Cited

U.S. PATENT DOCUMENTS

| | | | |
|---|---|---|---|
| 4,122,844 A * | 10/1978 | Rabban ............... 600/213 |
| D255,490 S | 6/1980 | Pastrick | |
| 4,570,624 A * | 2/1986 | Wu ..................... 606/96 |
| 4,955,885 A | 9/1990 | Meyers | |
| 5,217,463 A | 6/1993 | Mikhail | |
| 5,334,194 A | 8/1994 | Mikhail | |
| 5,380,331 A | 1/1995 | Mikhail | |
| 5,425,490 A * | 6/1995 | Goble et al. ......... 227/175.1 |
| 7,172,554 B2 * | 2/2007 | Gustke et al. ........... 600/213 |
| 7,195,593 B1 * | 3/2007 | Masson et al. .......... 600/235 |
| 2006/0074425 A1 * | 4/2006 | Sutterlin et al. ........ 606/79 |

OTHER PUBLICATIONS

Inomed Catalog, Orthopedic Instruments Including MIS Instruments & Techniques, pp. 76 and 79.

* cited by examiner

*Primary Examiner*—Thomas C Barrett
*Assistant Examiner*—Andrew Yang
(74) *Attorney, Agent, or Firm*—Lerner, David, Littenberg, Krumholz & Mentlik, LLP

(57) ABSTRACT

A ligament protector for use in protecting a ligament during an orthopedic procedure is disclosed. The ligament protector includes at least two wings and bone mounting elements. A handle may be removably coupled to the ligament protector.

39 Claims, 14 Drawing Sheets

LIGAMENT PROTECTION INSTRUMENTS

FIELD OF THE INVENTION

The present invention relates to orthopedic instruments for use during surgery, and more particularly, to a ligament protector and ligament protector assembly for protecting ligaments and/or other tissues during knee surgery.

BACKGROUND OF THE INVENTION

There is currently a trend towards performing orthopedic surgery utilizing minimally invasive techniques. For example, minimally invasive total knee arthroplasty is currently an emerging method of performing surgery of this type. While there are benefits to utilizing these minimally invasive surgical techniques (i.e.—quicker recovery time, less scarring, etc . . . ), there are also requirements and difficulties associated with the methods.

One standard step in many orthopedic procedures, whether minimally invasive or not, is the resection of a bone surface. For example, one of the steps in a knee arthroplasty is the resection of the proximal tibia. During a minimally invasive procedure on the tibia, it is necessary to protect the anterior cruciate ligament (ACL), the posterior cruciate ligament (PCL), or in certain cases, both. The lack of visibility and/or lack of operating space induced by the minimally invasive procedure makes protecting the ligaments even more difficult. Cutting these ligaments may force a surgeon to abandon his or her minimally invasive technique in favor of a more tradition surgical approach and require the use of stabilizing insert (e.g.—posterior stabilized insert or total stabilized insert).

For the foregoing reasons, there exists a need for a ligament protection device to protect the ligaments during a minimally invasive procedure.

SUMMARY OF THE INVENTION

A first aspect of the present invention is a ligament protection assembly. The ligament protection assembly according to this aspect includes a ligament protector having bone mounting means and a positioning instrument coupled with the ligament protector.

Another embodiment of the present invention is another ligament protection assembly. The ligament protection assembly according to this embodiment includes a ligament protector and a positioning instrument removably coupled with the ligament protector.

Another aspect of the present invention is a ligament protector including a substantially V-shaped body and bone mounting means.

Another embodiment of the present invention is another ligament protector. The ligament protector according to this embodiment includes at least two connected wings, means for mounting the ligament protector to a bone surface, and means for coupling the ligament protector to a positioning instrument. The wings are configured to allow for the engagement and protection of a ligament.

Yet another embodiment of the present invention is another ligament protector. The ligament protector according to this embodiment includes a body having a pair of wings each having sidewall with first and second ends wherein the sidewall second ends are spaced further apart than the first ends, and at least one pin extending from an upper or lower surface of each of the sidewalls for extending into a bone forming a part of the joint.

Yet another aspect of the present invention is a method of mounting a ligament protective device. The method according to this aspect includes the steps of providing a ligament protector having a body with sidewalls and a bone mounting means, inserting the ligament protector through an incision, positioning the ligament protector with respect to a ligament, and mounting the ligament protector onto a bone surface using the bone mounting means.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
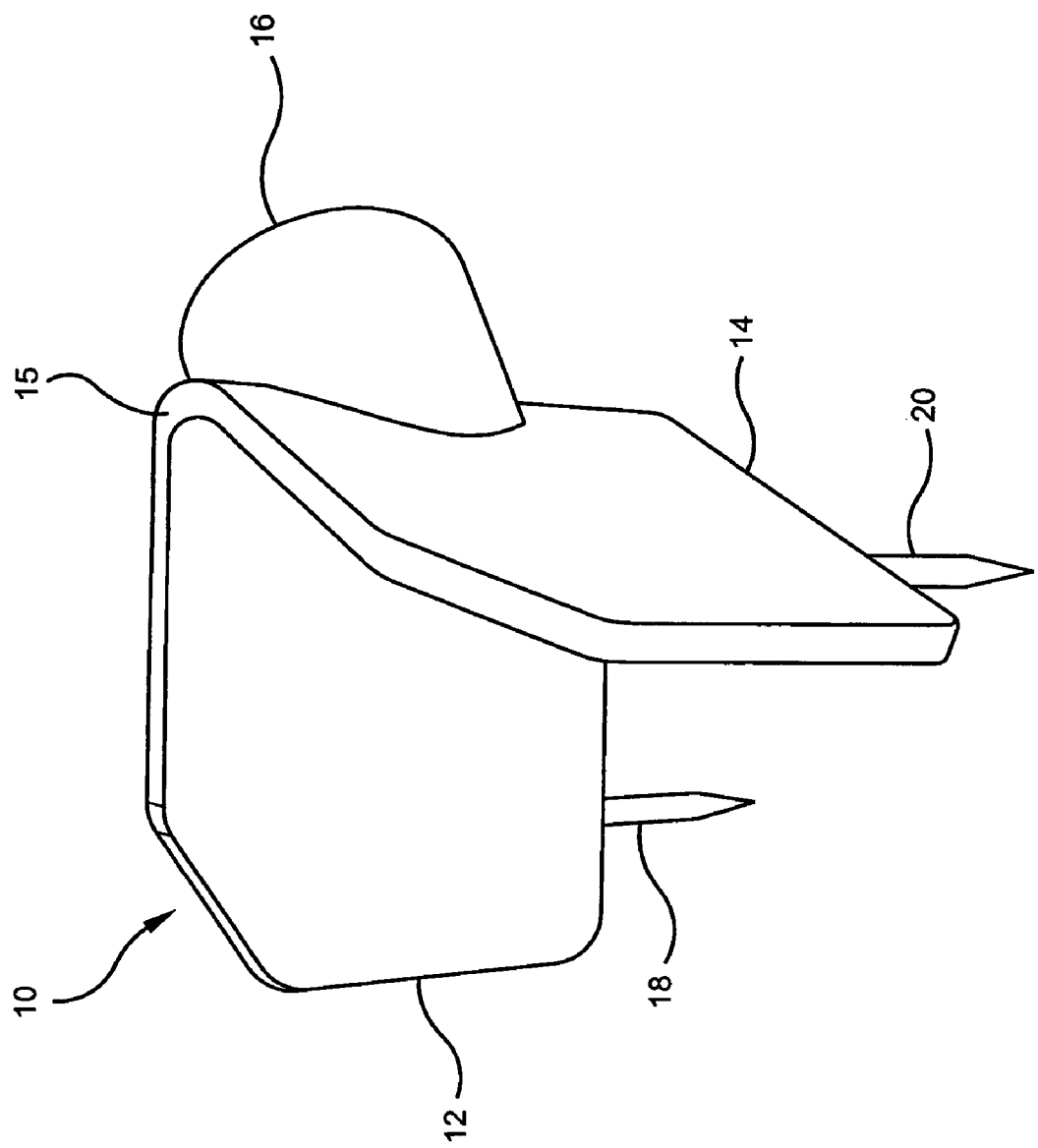
FIG. 1 is a top perspective view of the ligament protector according to an embodiment of the present invention.
Figure 2:
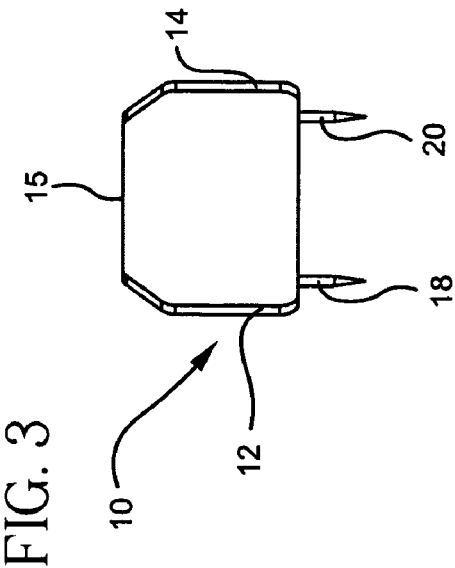
FIG. 2 is a plan view of the ligament protector according to FIG. 1.

In describing the preferred embodiments of the subject matter illustrated and to be described with respect to the drawings, specific terminology will be resorted to for the sake of clarity. However, the invention is not intended to be limited to the specific term and includes all technical equivalence which operates in a similar manner to accomplish a similar purpose.

Referring to the drawings, wherein like reference numerals represent like elements, there is shown in the Figures, in accordance with embodiments of the present invention, a ligament protector designated generally by reference numeral 10. In the embodiment shown in the Figures, ligament protector 10 is designed to be used in protecting either the anterior cruciate ligament or the posterior cruciate ligament during a knee arthroplasty. However, it is contemplated that other embodiments of the present invention can be designed for use in protecting different ligaments or other body tissue, during various procedures. As shown in FIGS. 1-4, ligament protector 10 is of unitary construction, and includes first wing 12, second wing 14, female connection 16, and spikes 18 and 20. In the preferred embodiment, wings 12 and 14 are 1-2 cm high and spaced 2-3 cm at their open ends.

First wing 12 and second wing 14 are arranged in a substantially V-shaped configuration. Essentially these wings are walls formed from rigid material and are spaced so as to be capable of receiving a ligament therebetween. First wing 12 and second wing 14 are rigidly connected to one another on their converging ends 15 on which female connection 16 also resides. It is contemplated that first wing 12 and second wing 14 could be moveably coupled (e.g.—rotatably coupled as by a hinge connection) to one another, so as to allow them to be manipulated with respect to each other. This embodiment of the ligament protector would allow for different sized ligaments to be more easily received between the wings. Similarly, it is also contemplated that other shaped configurations of the wings can be utilized. For example, a substantially U-shaped ligament protector may allow for the wings to more easily receive larger ligaments.

Figure 3:
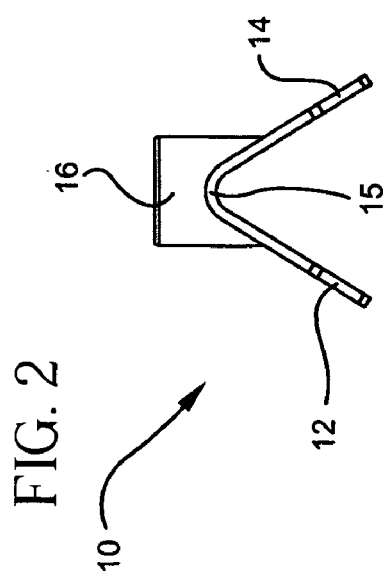
FIG. 3 is a front view of the ligament protector according to FIG. 1.
Figure 4:
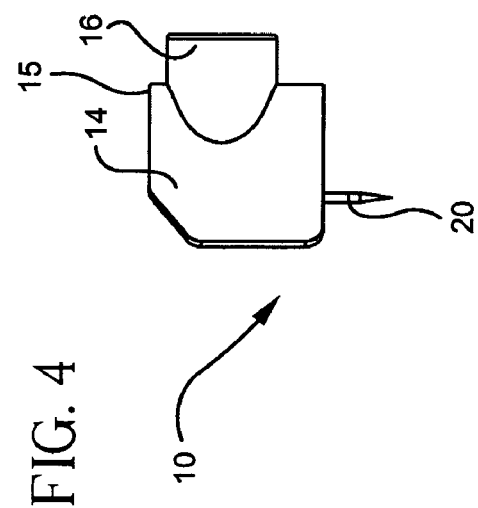
FIG. 4 is a right side view of the ligament protector according to FIG. 1.

As shown in FIGS. 1, 3, and 4, spikes 18 and 20 are elongate bodies having sharpened ends that allow for ligament protector 10 to be mounted to a bone surface. In accordance with the present invention, spikes 18 and 20 are dimensioned so that they are capable of being inserted into a bone to a depth suitable for holding ligament protector 10 in place. In a preferred embodiment, spikes 18 and 20 are approximately 1 cm in length, in order to facilitate this rigid mounting of ligament protector 10 to a bone such as the tibia. However, it is noted that spikes of other lengths may be sufficient. The embodiment of ligament protector 10 shown in the figures includes two spikes, 18 and 20. However, any number of spikes may be utilized. For example, certain embodiments of the present invention include a ligament protector 10 having three spikes. The addition of more spikes would allow for a more rigid mounting of ligament protector 10 to a bone surface. Similarly, other attaching means can be utilized for attaching ligament protector 10 to a bone surface. For example, screws or pins may be inserted through apertures located on wings 12 and 14, or adhesive may be employed to fixably attach ligament protector 10.

Figure 5:
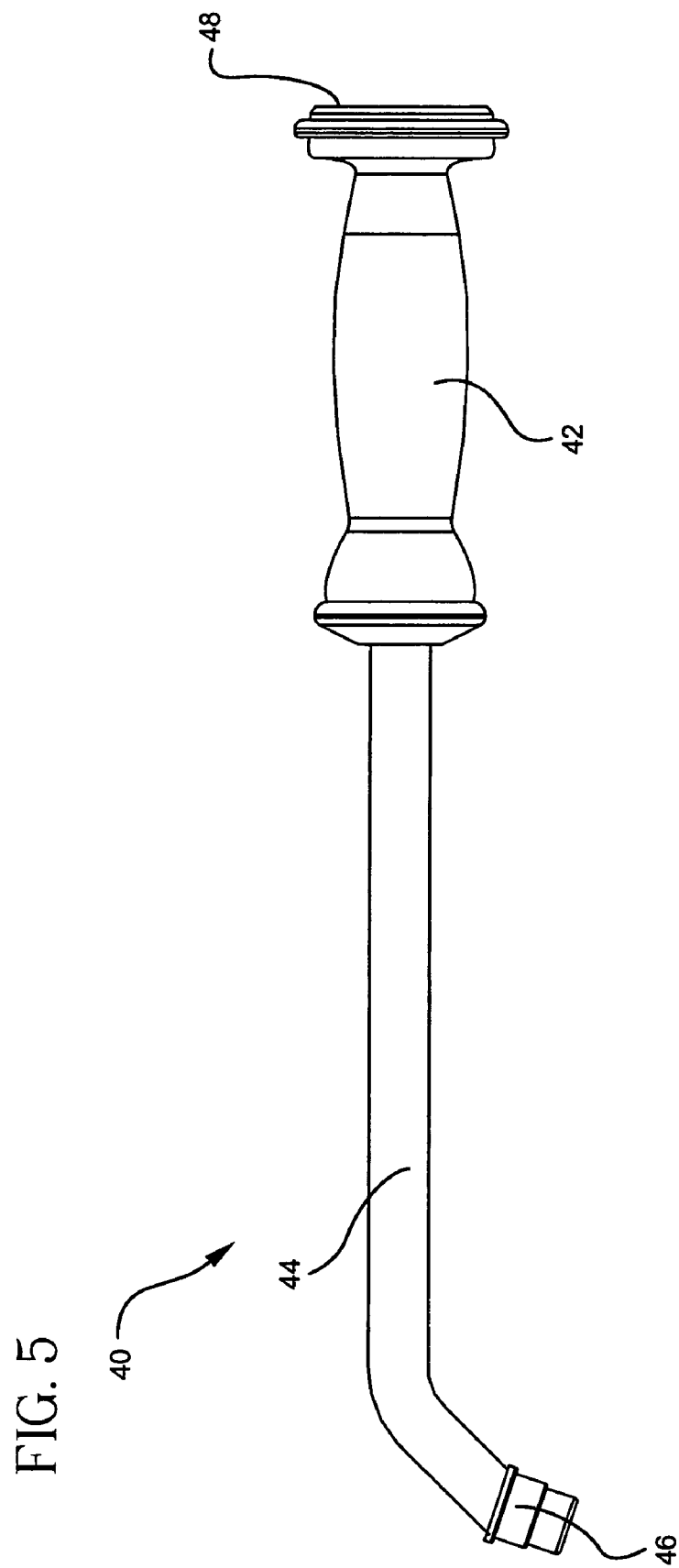
FIG. 5 is a side view of the positioning instrument according to an embodiment of the present invention.

FIG. 5 shows a positioning instrument 40 for aligning and placing ligament protector 10. As shown in the Figure, positioning instrument 40 includes handle 42, elongate shaft 44, and a male connection 46. Handle 42 is a standard handle device preferably dimensioned and configured to be grasped by the hand of a surgeon. Optionally, handle 42 may be ergonomically designed to be of optimal shape for grasping by a human hand. The gripping portion of handle 42 is preferably constructed of a rubber material suitable for providing a non-slip grip, but may be any other material suitable for this function. In the preferred embodiment shown in the Figures, handle 42 includes an impaction pad 48 designed to aid in mounting ligament protector 10 to a bone surface. This will be discussed in more detail below. Elongate shaft 44 provides a structural connection between handle 42 and male connection 46. In the embodiment shown in FIG. 5, elongate shaft 44 has handle 42 connected on one side and male connection 46 on the other. In the preferred embodiment shown in the Figures, elongate shaft 44 is bent to allow for easier placement of ligament protector 10. It is contemplated that elongate shaft 44 may be dimensioned and configured in different fashions, in order to facilitate the placement and connection of ligament protector 10 in different areas of the body. For example, shaft 44 may be long and bent (as shown in the drawings) to place ligament protector 10 during a knee surgery, but of different configuration and dimensions for placement of ligament protector 10 during other surgical approaches.

Figure 6:
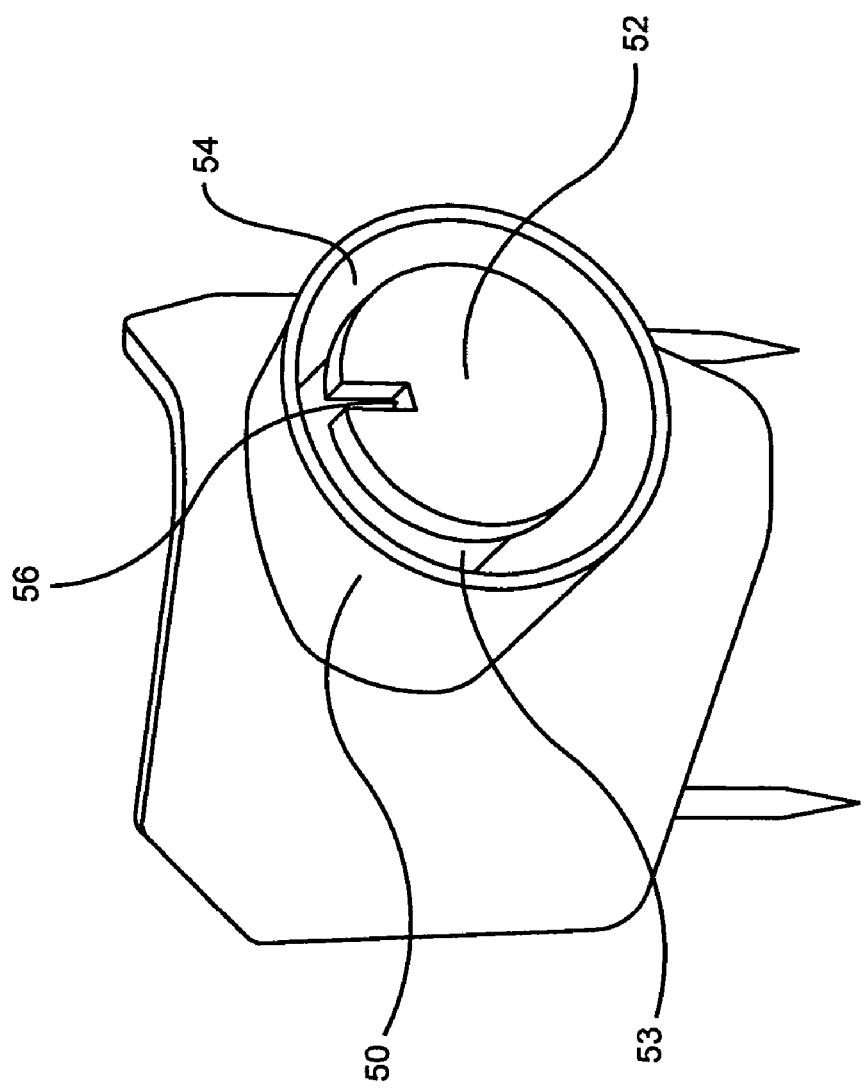
FIG. 6 is a rear perspective view of the ligament protector according to FIG. 1.
Figure 7:
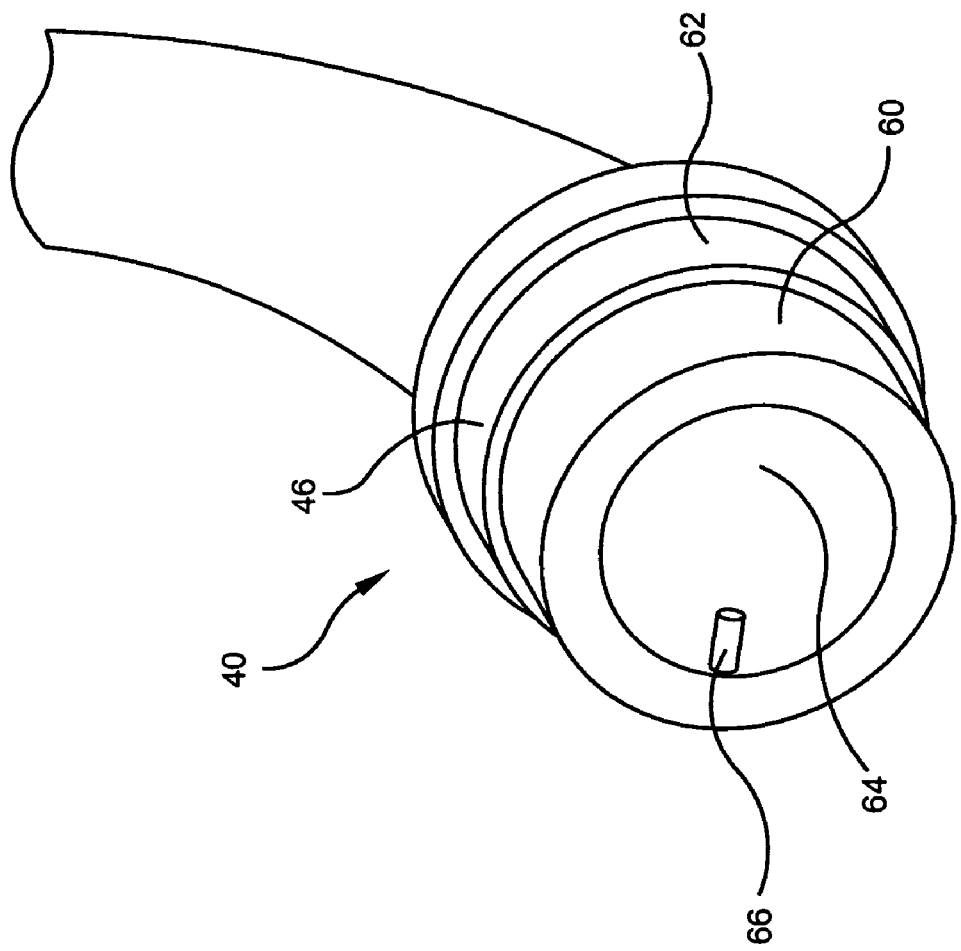
FIG. 7 is a perspective view of the male connection of the positioning instrument of FIG. 5 for mating with the ligament protector according to FIG. 1.

Protector 10 and instrument 40 are connected by a bayonet type coupling. In the preferred embodiment, male connection 46 is designed to cooperate with female connection 16 of ligament protector 10. Detail of the female connection 16 and male connection 46 are shown in FIGS. 6 and 7, respectively. Female connection 16 is a circular protrusion having exterior wall 50, raised interior platform 52, circular channel 54, and notch or keyway 56 formed in the interior structure 52. As mentioned above, female connection resides on the end at which first wing 12 and second wing 14 connect to one another. Male connection 46 is a circular protrusion having a first wall 60, a second wall 62, a hollow interior 64, and a key section 66.

Figure 8A:
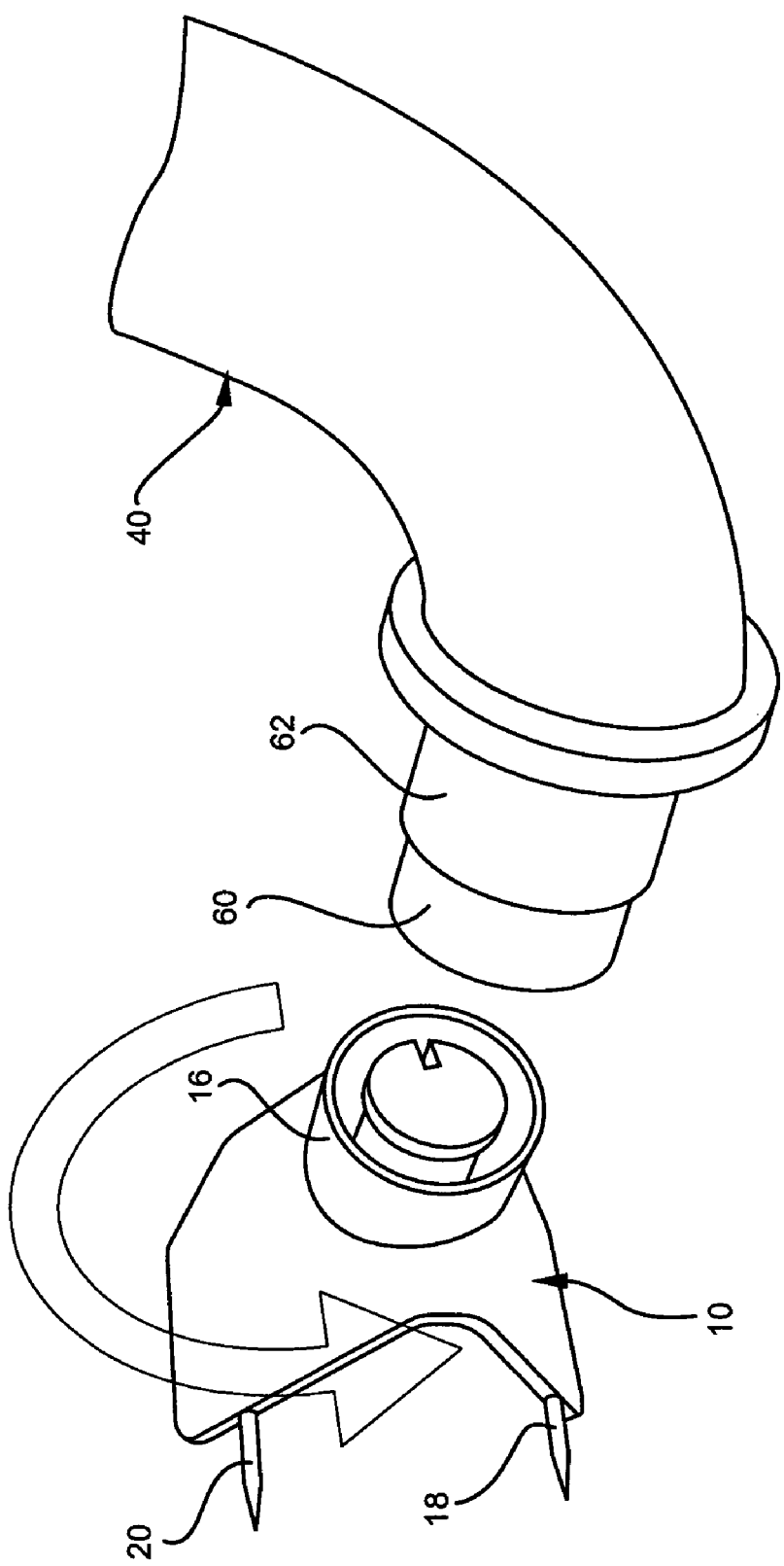
FIGS. 8a and 8b show a structure for attaching the positioning instrument of FIG. 5 to the ligament protector of FIG. 1.
Figure 8B:
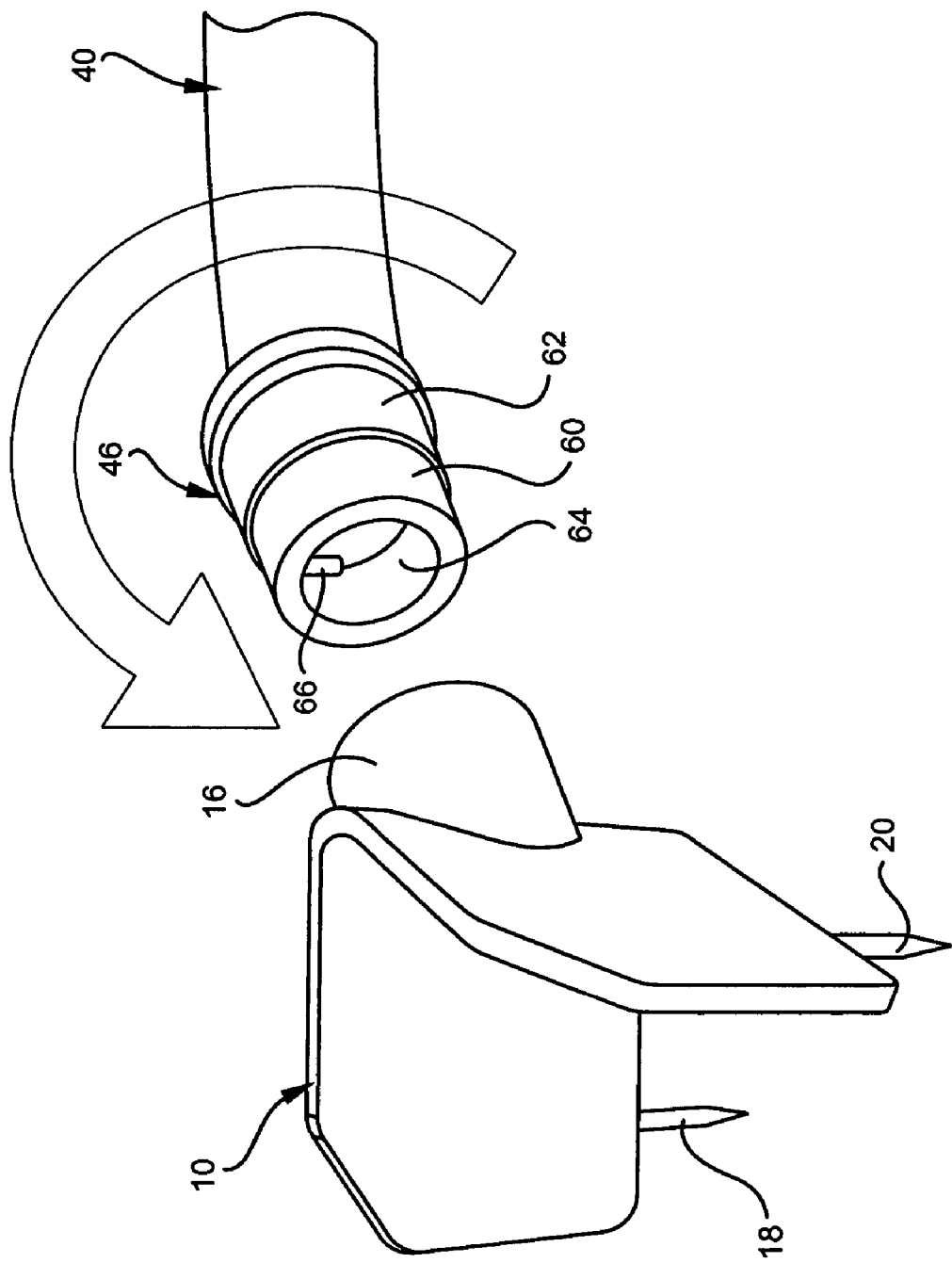
Figure 9:
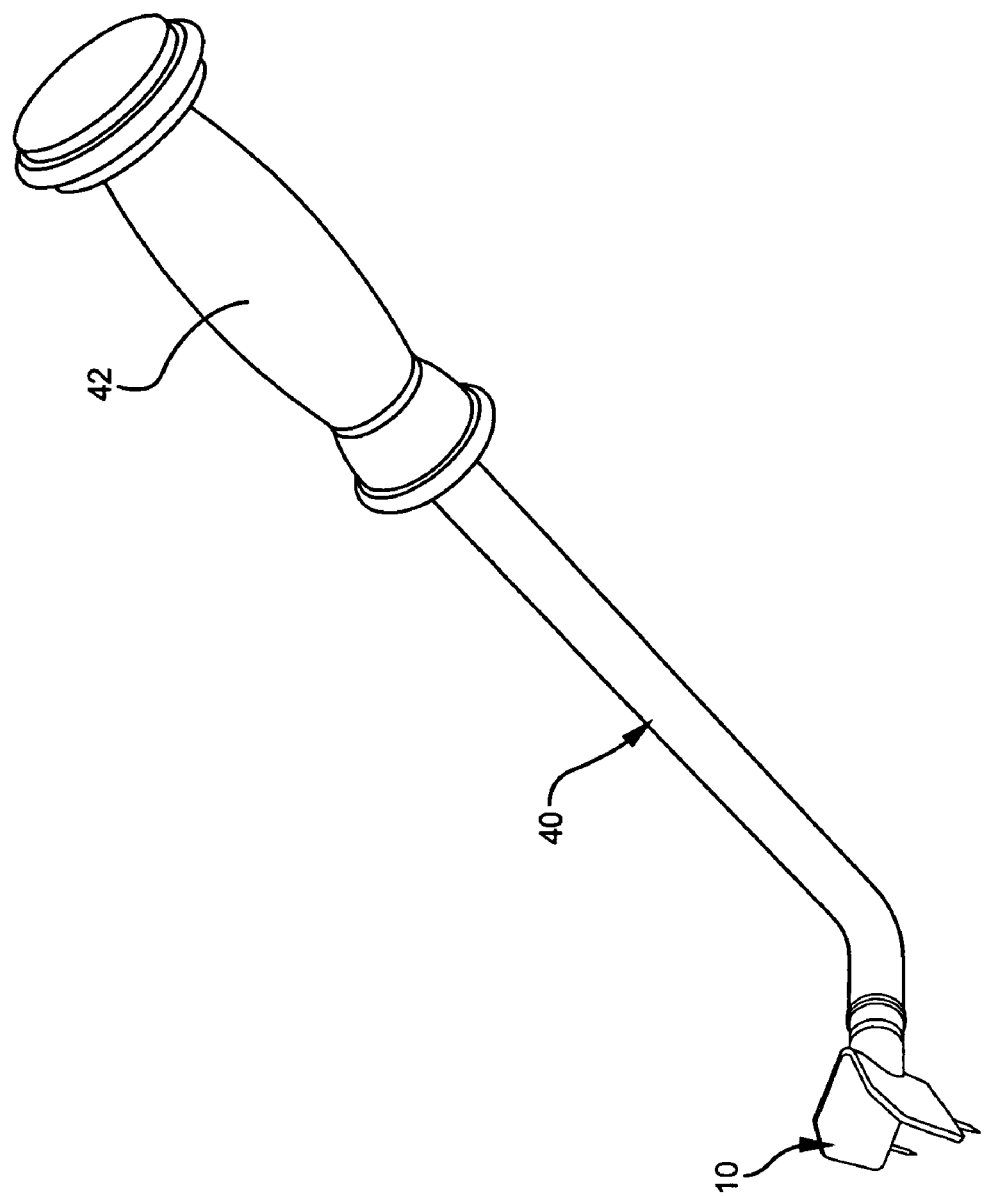
FIG. 9 is a perspective view of the positioning instrument of FIG. 5 attached to the ligament protector of FIG. 1.

It is contemplated that first wall 60 is dimensioned so as to fit into circular channel 54. Similarly, hollow interior 64 is dimensioned so as to be capable of receiving raised interior platform 52. It should be noted that second wall 62 has too large of a diameter to allow it to fit within circular channel 54 and acts as a stop surface. In operation, first wall 60 is inserted into circular channel 54 in a manner that aligns key section 66 and notch 56. In this inserted position the raised configuration of platform 52 allows for key section 66 to sit below the underside of platform 52 in channel 53. This channel is dimensioned to allow key section 66 to rotate beneath platform 52. As best shown in FIG. 8a, the additional step of rotating either ligament protector 10 or positioning instrument 40, with respect to one another, approximately a quarter turn to essentially offset or non-aligned key section 66 and notch 56 is then performed. In this misaligned position, key section 66 is trapped in channel 53, and ligament protector 10 and positioning instrument 40 are attached to one another, as best shown in FIG. 9. Similarly, as shown in FIG. 8b, an approximate quarter turn the opposite way realigns key section 66 and notch 56, thereby allowing for the removal of ligament protector 10 from positioning instrument 40.

Figure 10:
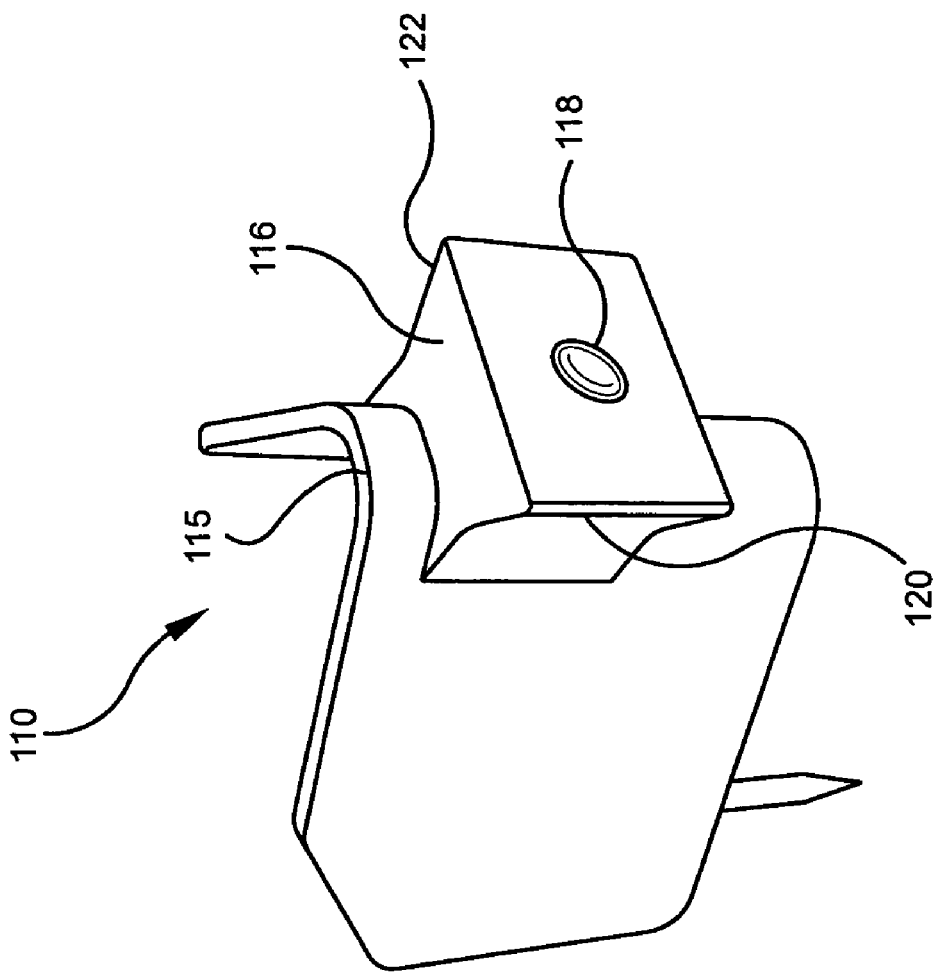
FIG. 10 is a rear perspective view of a ligament protector according to another embodiment of the present invention.
Figure 11:
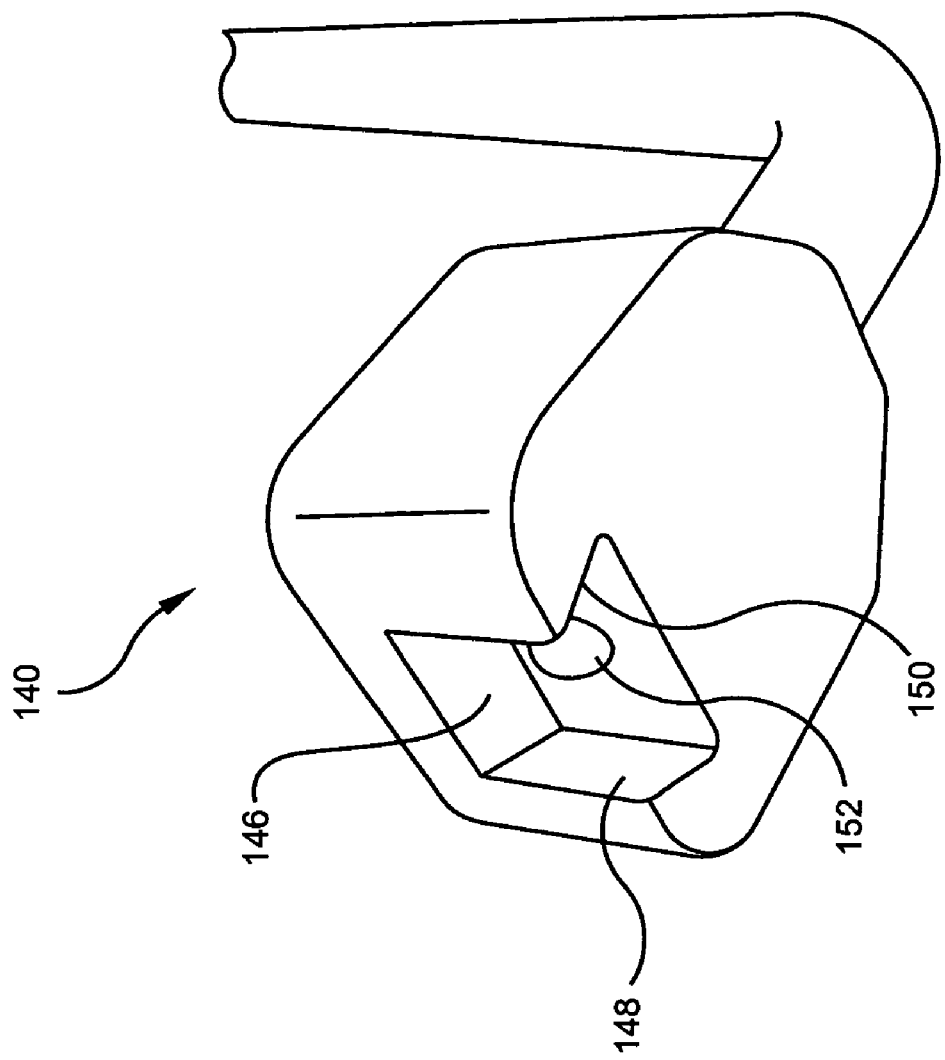
FIG. 11 is a perspective view of the connection of the positioning instrument for mating with the ligament protector according to FIG. 10.

Another embodiment of the manner of connection of the ligament protector and the positioning instrument is shown in FIGS. 10-15. In this embodiment, ligament protector 110 includes a male dovetail connection 116, while positioning instrument 140 includes a female dovetail connection 146. As shown in FIG. 10, male dovetail connection 116 includes aperture 118 and dovetailed walls 120 and 122. Male connection 116 is dimensioned and configured to be received between dovetailed walls 148 and 150 of female connection 146, as shown in FIG. 11. It is noted that female connection 146 also includes rounded protrusion 152, dimensioned and configured to fit within aperture 118.

Figure 12:
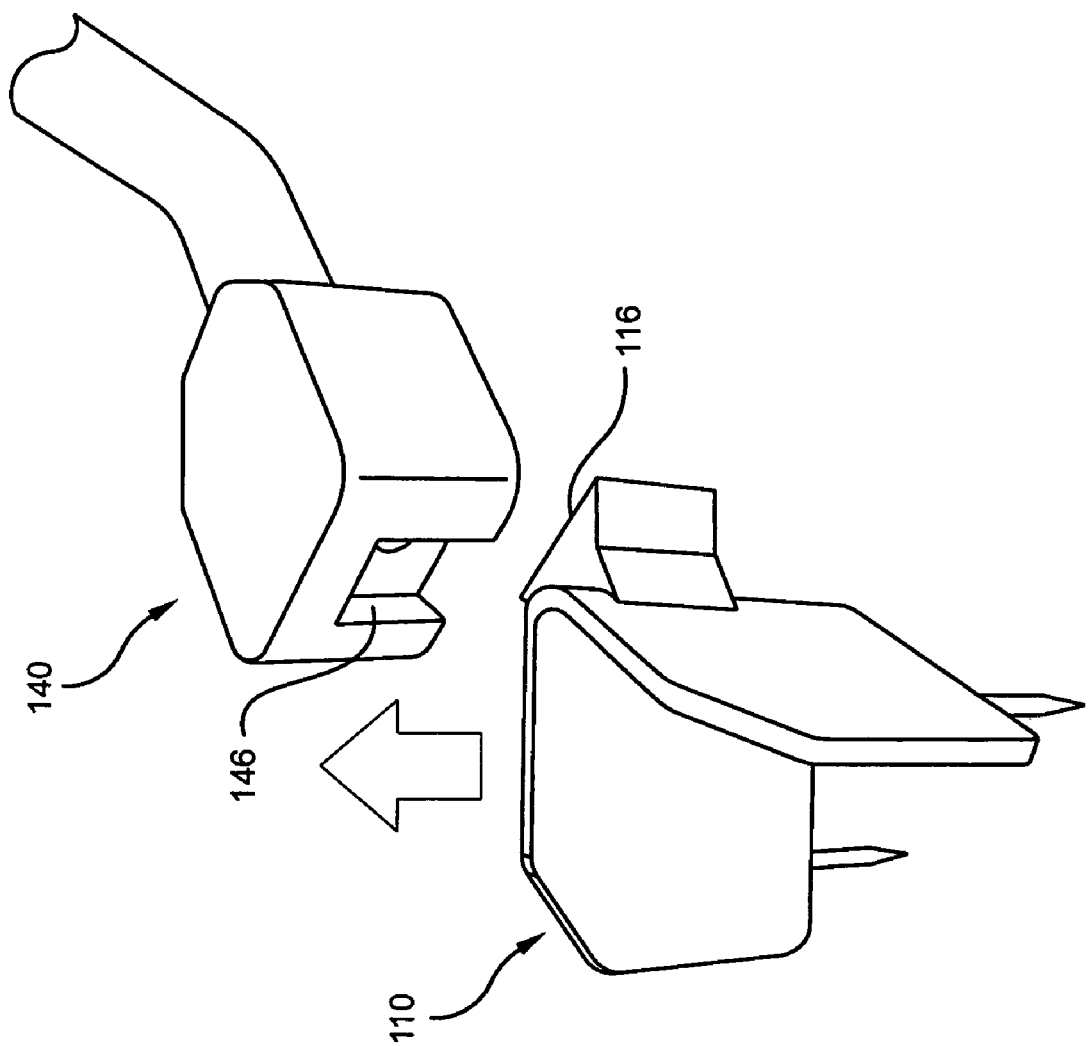
FIG. 12 is a perspective view depicting the method of connecting the ligament protector of FIG. 10 to the positioning instrument of FIG. 11.
Figure 13:
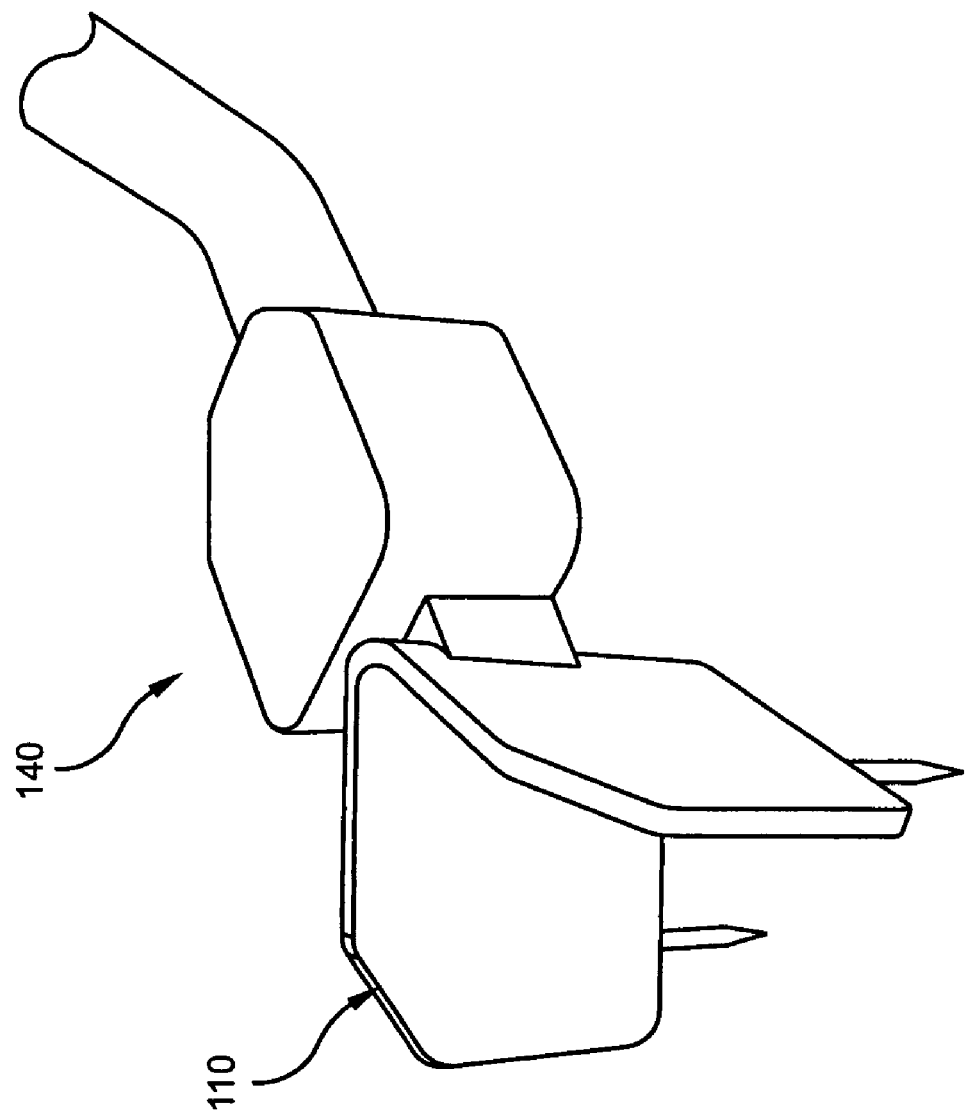
FIG. 13 is a perspective view of the ligament protector of FIG. 10 connected to the positioning instrument of FIG. 11.

In operation, as shown in FIG. 12, female connection 146 is slid over male connection 116. The dovetailed shape of their respective walls prevents ligament protector 110 from being removed from positioning instrument 140 in an anterior posterior direction. Similarly, the cooperation of aperture 118 and rounded protrusion 152 prevents removal in the proximal distal direction. FIG. 13 illustrated a connected ligament protector 110 and positioning instrument 140. It is contemplated that removal of positioning instrument 140 from ligament protector 110 requires the manipulation of female connection 146 in a manner that disengages rounded protrusion 152 from aperture 118. Upon successful disengagement, female connection 146 can be slide away from male connection 116. Certain embodiments may include a rounded protrusion that is a spring loaded ball detent, that allows for easier engagement and disengagement of ligament protector 110 and positioning instrument 140.

Another aspect of the present invention is a method for mounting ligament protector 10 or similarly the aforementioned ligament protector 110. This method provides the steps necessary to properly protect either the ACL or PCL during a minimally invasive knee procedure. It is contemplated however, that the method in accordance with the present invention could be tailored to protect any ligament or other body structure within the body. The method according to this aspect of the invention includes the step of providing a ligament protector 10 as discussed above. It is contemplated that a ligament protector can be provided in accordance with any of the various embodiments discussed above (e.g.—ligament protector 110), and can be combined with the aforementioned positioning instrument 40 (or positioning instrument 140) in order to provide a ligament protector assembly for more easily facilitating the placement of the ligament protector. However, it is contemplated, that ligament protector 10 can also be inserted by other means than that of the previously discussed positioning instrument 40 or even by hand. Ligament protector 10 is inserted through an incision made during the normal course of the surgical operation. In the preferred embodiment, the incision is a relatively small incision typical of a minimally invasive procedure. Such an incision may range from approximately 4 cm to 10 cm.

Once ligament protector 10 is inserted through the incision, it should be aligned so that a ligament (in the case of knee surgery, either the ACL or PCL) is situated between wings 12 and 14. With this ligament essentially captured between wings 12 and 14, ligament protector 10 can be manipulated to displace the captured ligament to a position that is safely out of the way of the pending bone cut. Irregardless of this position, the construction of ligament protector 10 should be capable of deflecting an errant cutting instrument. When this position is achieved, ligament protector 10 is mounted to any adjacent bone surface. For example, when protecting the ACL, ligament protector 10 is mounted to the anterior proximal side of the tibia (shown in FIGS. 14 and 15), and when protecting the PCL, ligament protector 10 is mounted to the posterior proximal side of the tibia. The orientation of ligament protector 10 is such that the open end created by wings 12 and 14 faces away from the surface of the bone to be cut, thus aligning the closed end 15 (the end at which wings 12 and 14 are connected to one another) adjacent to the bone cut and thus, the bone cutting instrument. This provides a closed structure that protects the captured ligament.

Figure 14:
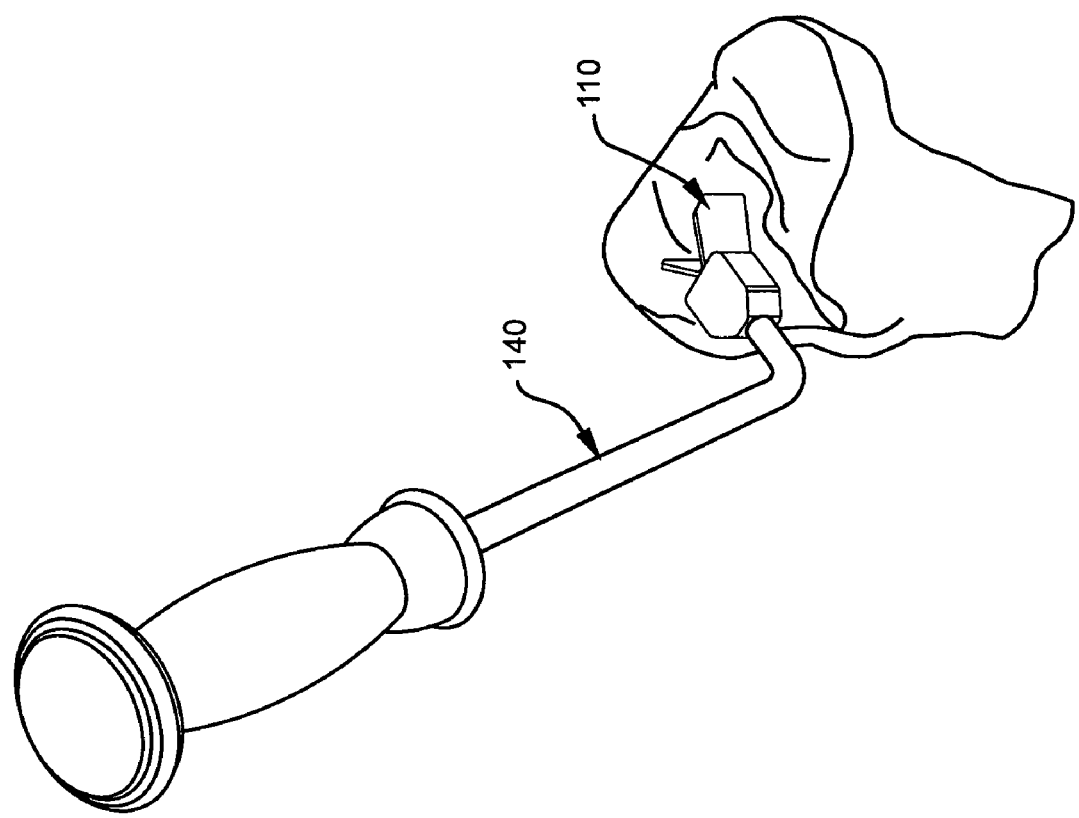
FIG. 14 is a perspective view depicting the method of attaching a ligament protector according to the present invention to a tibia.
Figure 15:
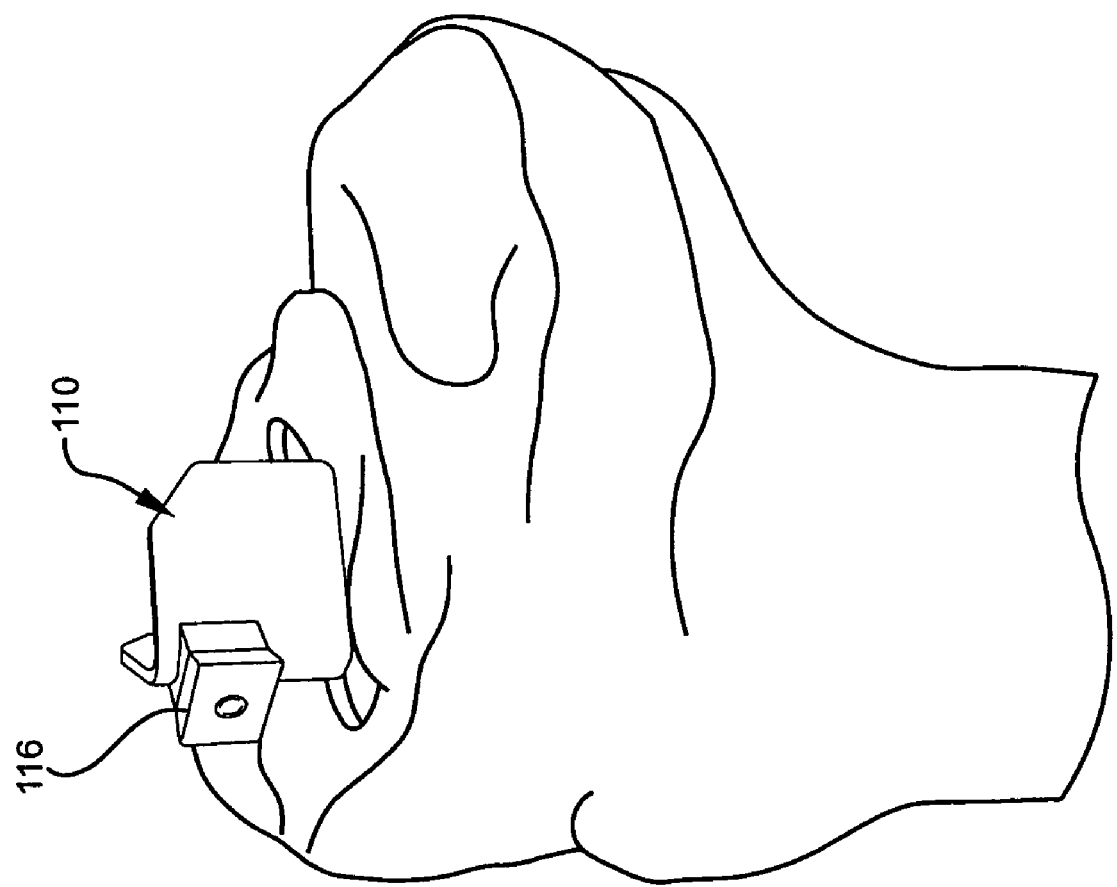
FIG. 15 is a perspective view of a ligament protector according to the present invention attached to the tibia.

FIG. 14 shows a coupled ligament protector and positioning instrument just prior to the fixable mounting of the ligament protector to the bone surface. In order to mount ligament protector 10 to the bone surface, a downward force must be applied to the protector to sink or embed spikes 18 and 20 into the bone. A surgeon may simply utilize his or her own strength and push spikes 18 and 20 into the bone, or most preferably utilize the aforementioned impaction pad 48. To utilize the latter, a surgeon applies a blunt force to impaction pad 48 with an instrument such as a hammer or mallet. Essentially, with ligament protector 10 in a position in which spikes 18 and 20 are in contact or adjacent the bone surface, the surgeon hits impaction pad 48, thereby transferring the force from pad 48, along shaft 42, to ligament protector 10. One or more hits of the instrument may be required in order to rigidly mount protector 10 in the desired position.

Subsequent to mounting ligament protector 10 to the bone surface, positioning instrument 40 may be removed. This prevents positioning instrument 40 from hindering the remaining steps in the surgical procedure. As discussed above, approximately one quarter of a turn (in the opposite direction from that performed to attach positioning instrument 40 to ligament protector) and a retraction force applied to positioning instrument 40 away from ligament protector 10, will remove positioning instrument 40. It is contemplated that in other embodiments that utilize different embodiments discussed above, the removal of positioning instrument 140 from ligament protector 110 may also be performed in accordance with the procedure discussed above. For example, disengaging rounded protrusion 152 and separating the dovetailed connectors from one another. With ligament protector 10 in place its orientation will deflect any cutting device that may inadvertently contact it. It is contemplated that more than one ligament protector can be utilized at one time. For example, in the case of minimally invasive knee surgery, one protector could be mounted to protect the ACL and another could be mounted to protect the PCL. In this case, each ligament protector 10 would be mounted on opposite sides of the tibia, and have opposite orientations facing away from each other.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of mounting a ligament protective device comprising:
   providing a ligament protector having a body with first and second wings and a bone mounting means;
   coupling said ligament protector with a positioning instrument;
   inserting said ligament protector through an incision;
   positioning said ligament protector with respect to a ligament so that the ligament is captured between the first and second wings;
   mounting said ligament protector onto a bone surface using said bone mounting means;
   uncoupling said positioning instrument from said ligament protector, wherein said uncoupling step includes rotating said positioning instrument; and
   removing said ligament protector from said bone surface.

2. The method according to claim 1, wherein said coupling step is performed prior to said inserting step.

3. The method according to claim 2, wherein said mounting step includes manipulating the positioning instrument to engage the bone mounting means with the bone surface.

4. The method according to claim 3, wherein the bone mounting means are spikes.

5. The method according to claim 4, wherein a force is applied to the positioning instrument to insert the spikes in the bone surface.

6. The method according to claim 5, wherein said positioning instrument includes an impaction pad for reception of the force.

7. The method according to claim 1, wherein said ligament protector is substantially V-shaped.

8. The method according to claim 1, wherein said bone mounting means are spikes.

9. The method according to claim 1, wherein said incision is less than 10 cm in length.

10. The method according to claim 1, wherein said positioning step includes positioning said ligament protector with respect to a PCL.

11. The method according to claim 1, wherein said positioning step includes positioning said ligament protector with respect to an ACL.

12. The method according to claim 1, further including the step of removing the positioning instrument from the incision.

13. The method according to claim 1, wherein said ligament protector includes one of a male connection or a female connection and said positioning instrument includes the other of the male connection or the female connection.

14. The method according to claim 1, wherein said inserting, positioning, and mounting steps are performed utilizing said positioning instrument.

15. The method according to claim 1, further comprising the step of displacing the ligament.

16. The method according to claim 1, further comprising the step of making a bone cut subsequent to said uncoupling step.

17. The method according to claim 1, wherein said first and second wings are attached directly to each other.

18. The method according to claim 1, wherein the first wing includes first and second ends and the second wing includes third and fourth ends, and the first and third ends are attached.

19. The method according to claim 18, wherein the first and third ends are attached via a connection.

20. The method according to claim 19, wherein said coupling step includes engaging said positioning instrument with the connection.

21. The method according to claim 20, wherein said positioning instrument includes a grip and a shaft.

22. The method according to claim 1, further comprising the step of manipulating the first and second wings with respect to each other.

23. The method according to claim 1, wherein said removing step includes coupling said positioning instrument to said ligament protector and manipulating said positioning instrument to remove said ligament protector.

24. A method of protecting a ligament comprising:
 providing a ligament protector having first and second wings coupled to each other and a connection, the first and second wings forming an open end;
 manipulating the first and second wings with respect to each other to vary the open end;
 coupling the connection with a positioning instrument;
 capturing the ligament in the open end;
 mounting the ligament protector to a bone surface;
 uncoupling the positioning instrument from the connection; and
 removing the ligament protector from the bone surface.

25. The method according to claim 24, further comprising the step of inserting the ligament protector through an incision.

26. The method according to claim 24, wherein the ligament protector is V-shaped.

27. The method according to claim 24, wherein the ligament protector further includes bone mounting means and the mounting step includes engaging the bone mounting means with the bone surface.

28. The method according to claim 27, wherein the bone mounting means are spikes.

29. The method according to claim 24, wherein the positioning step includes positioning the ligament protector with respect to an ACL or a PCL in the knee.

30. The method according to claim 24, wherein the positioning step includes manipulating the positioning instrument.

31. The method according to claim 24, wherein the mounting step includes applying a force to the positioning instrument.

32. The method according to claim 31, wherein the applying step includes applying a force to an impaction pad of the positioning instrument.

33. The method according to claim 24, further comprising the step of displacing the ligament.

34. The method according to claim 24, further comprising the step of making a bone cut subsequent to the uncoupling step.

35. The method according to claim 24, wherein the first and second wings are attached directly to each other.

36. The method according to claim 24, wherein the connection is a male connection or a female connection and the positioning instrument includes the other of the male connection or female connection and the coupling step includes coupling the particular connections.

37. The method according to claim 36, wherein said coupling and uncoupling steps includes rotating the positioning instrument.

38. The method according to claim 24, wherein the removing step includes coupling the positioning instrument to the ligament protector and manipulating the positioning instrument to remove the ligament protector.

39. A method of performing surgery comprising:
 providing a ligament protector having first and second wings forming an open end, a connection attached to the first and second wings, a first spike extending from the first wing, and a second spike extending from the second wing;
 coupling the connection with a positioning instrument;
 capturing a ligament in the open end;
 inserting the first and second spikes into a bone surface to fix the ligament protector thereto;
 uncoupling the positioning instrument from the connection;
 cutting a bone while the ligament protector is fixed to the bone surface;
 recoupling the positioning instrument to the connection; and
 removing the ligament protector from the bone.

* * * * *